US00PP24076P2

(12) United States Plant Patent
Andrusiv

(10) Patent No.: US PP24,076 P2
(45) Date of Patent: Dec. 10, 2013

(54) ***BERBERIS* PLANT NAMED 'ORANGE DREAM'**

(50) Latin Name: *Berberis thunbergii*
Varietal Denomination: Orange Dream

(75) Inventor: Michal Andrusiv, Litomyal (CZ)

(73) Assignee: Valk Plants B.V., Boskoop (NL)

( * ) Notice: Subject to any disclaimer, the term of this patent is extended or adjusted under 35 U.S.C. 154(b) by 93 days.

(21) Appl. No.: 13/506,333

(22) Filed: Apr. 12, 2012

(51) Int. Cl.
*A01H 5/00* (2006.01)

(52) U.S. Cl.
USPC ..... Plt./241

(58) Field of Classification Search
USPC ..... Plt./241
See application file for complete search history.

*Primary Examiner* — Susan McCormick Ewoldt
(74) *Attorney, Agent, or Firm* — Penny J. Aguirre

(57) ABSTRACT

A new cultivar of *Berberis*, 'Orange Dream', that is characterized by its small sized leaves that are gray-purple to brown in color and its upright, broadly spreading plant habit with branches arching.

2 Drawing Sheets

Botanical classification: *Berberis thunbergii.*
Cultivar designation: 'Orange Dream'.

RELATED APPLICATIONS

This application is with U.S. Plant Patent applications filed for cultivars derived from the same breeding program entitled *Berberis* Plant Named 'Golden Dream' (U.S. Plant application Ser. No. 13/506,337) and *Berberis* Plant Named 'Red Dream' (U.S. Plant application Ser. No. 13/506,332).

BACKGROUND OF THE INVENTION

The present invention relates to a new and distinct cultivar of *Berberis thunbergii*, and will be referred to hereafter by its cultivar name, 'Orange Dream'. 'Orange Dream' is grown for use as a landscape shrub.

The new cultivar arose through an ongoing breeding project by the Inventor in Litomysl, Czech Republic with the objective of selecting new and unique cultivars of *Berberis*. 'Orange Dream' arose from open pollination in 2003 of an unnamed plant of *Berberis thunbergii* from the Inventors breeding program as the female parent. 'Orange Dream' was selected as a single unique plant from the resulting seedlings in 2005.

Asexual reproduction of the new cultivar was first accomplished by the Inventor by softwood stem cuttings in Litomysl, Czech Republic in 2007. It has been determined that the characteristics of this cultivar are stable and are reproduced true to type in successive generations.

SUMMARY OF THE INVENTION

The following traits have been repeatedly observed and represent the characteristics of the new cultivar, which in combination distinguish 'Orange Dream' as a new and distinct cultivar of *Berberis.*

1. 'Orange Dream' exhibits small sized leaves.
2. 'Orange Dream' exhibits foliage that is gray-purple to brown in color.
3. 'Orange Dream' exhibits on upright, broadly spreading plant habit with branches arching.

The female parent of 'Orange Dream' differs from 'Orange Dream' in having dark green leaves, a more open growth habit, and broader and larger leaves. 'Orange Dream' can be most closely compared to the cultivars 'Golden Dream', 'Red Dream' 'Admiration' (U.S. Plant Pat. No. 16,921), and 'Aurea' (not patented). 'Golden Dream' differs from 'Orange Dream' in having yellow-green leaves, a more compact plant habit, and branches that are upright rather than branching. 'Red Dream' differs from 'Orange Dream' in having leaves that are even more brown in color. 'Admiration' differs from 'Orange Dream' in having broader larger leaves that are gray-purple to orange-brown in color with thin yellow-green margins and in having a more compact dense plant habit. 'Aurea' differs from 'Orange Dream' in having yellow leaves and a more compact plant habit.

BRIEF DESCRIPTION OF THE DRAWING

The accompanying colored photographs illustrate the overall appearance and distinct characteristics of the new *Berberis*. The photographs were taken of a plant two years in age as grown in a one-gallon container in Helden, The Netherlands.

The photograph in FIG. 1 provides a view of the plant habit of 'Orange Dream' and The photograph in FIG. 2 provides a close-up view of the foliage of 'Orange Dream'.

Figure 1:
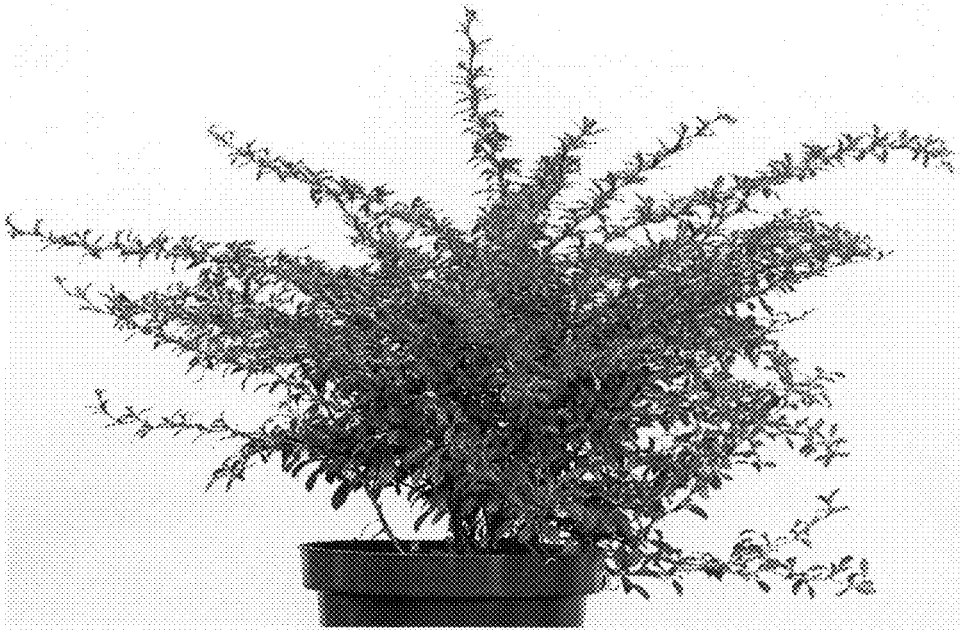
Figure 2:
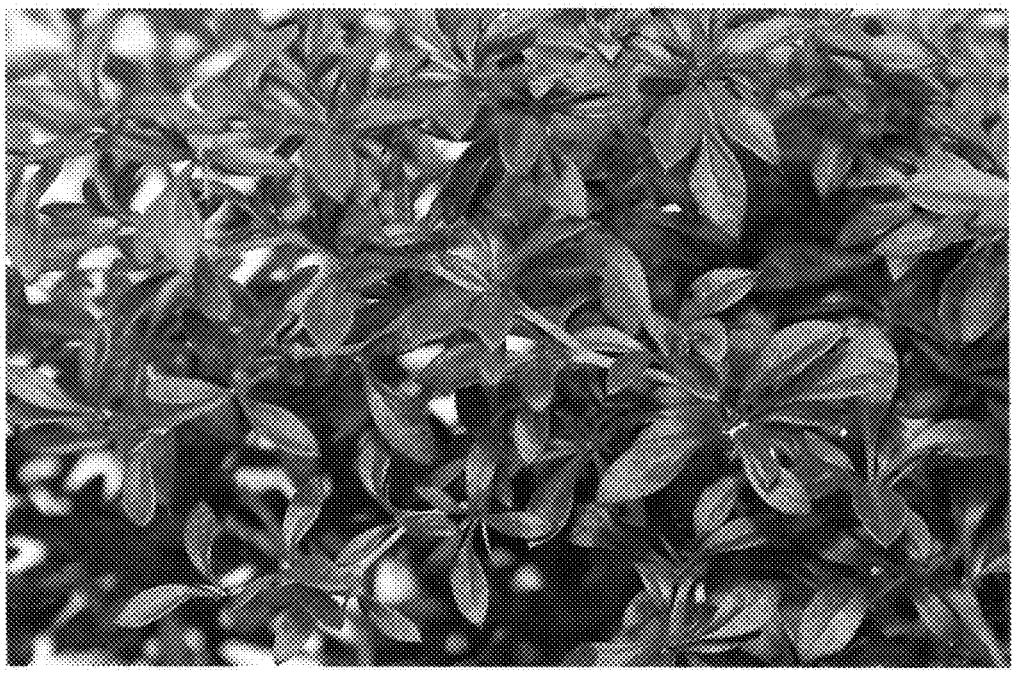

The colors in the photographs may differ slightly from the color values cited in the detailed botanical description, which accurately describe the colors of the new *Berberis.*

DETAILED BOTANICAL DESCRIPTION OF THE PLANT

The following is a detailed description of two year-old plants of the new cultivar as grown in one-gallon containers in Heiden, The Netherlands. Plants were grown under average day temperatures of 15° C. and average night temperatures of 10° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General plant characteristics:

*Plant type.*—Perennial deciduous shrub.

*Plant habit.*—Upright and broadly spreading with arching branches.

*Height and spread.*—Reaches about 29 cm in height and 56 cm in width in a one-gallon container.

*Cold hardiness.*—Hardy to at least U.S.D.A. Zone 5.

*Disease resistance.*—Not more susceptible to pests and diseases than other *Berberis.*

*Root description.*—Fibrous, moderate to densely branched.

*Growth rate.*—Moderate.

*Propagation.*—Softwood stem cuttings.

*Rooting.*—Initiate in 28 to 36 days at 17° C. air temperature, a young fully rooted plant is produced in 28 to 36 days at 17 to 19° air temperature (summer).

Stem description:

*Stem size.*—Lateral branches are an average of 22.6 cm in length and 2 mm in diameter.

*Stem shape.*—Round.

*Stem color.*—Young shoots upper surface; 179A, later turning 174A to 174B, young shoots lower surface; 179A, later turning 151B to 151C, mature stems both surfaces; 200B to 200C.

*Stem surface.*—Upper side; dull, lower side; moderately glossy and axially ribbed.

*Stem strength.*—Strong.

*Internode length.*—Average of 8 mm.

*Branching habit.*—Moderate to high with an average of 68 lateral branches.

*Branching aspect.*—Lateral branches an average angle of 45° (vertical=0°), branch tips near horizontal due to arching of branches.

Foliage description:

*Leaf shape.*—Oblanceolate to obovate.

*Leaf division.*—Simple.

*Leaf base.*—Long attenuate.

*Leaf apex.*—Acute.

*Leaf venation.*—Pinnate.

*Leaf margins.*—Entire.

*Leaf attachment.*—Sessile.

*Leaf arrangement.*—Alternate, clustered.

*Leaf surface.*—Upper surface; smooth and moderately glossy, lower surface; dull.

*Leaf color.*—Upper surface immature foliage; 175A, lower surface immature foliage; 177C, mature foliage upper surface; a color between 186C and 200B, leaves at base of lateral branches in the shade ("inside" the plant) turn 137B, mature lower surface foliage; 182B, flushed with 147C, leaves at base of lateral branches in the shade ("inside" the plant) turn 138B.

*Leaf number.*—Average of 6 per cluster at each node, 170 leaves per lateral branch.

*Leaf size.*—Average of 1.7 cm in length and 0.5 cm in width.

*Leaf aspect.*—Held upward at about a 45° angle.

*Leaf veins.*—Upper surface; between N186C and 200B, leaves at base of lateral branches in the shade ("inside" the plant) turn 137B, lower surface; 144B, leaves at base of lateral branches in the shade ("inside" the plant) turn 144B.

*Petioles.*—No petioles present.

*Thorn.*—Below each node is a sharp single thorn; average of 7 mm length and 1 mm in width at base, color; upper side; 172B, under side; 151A, tip; 200A, mature thorns; 200A.

Flower description:

*Flowering.*—No flowers have been observed, considered non-flowering.

*Fruit and seed.*—Seed production has not been observed.

It is claimed:

1. A new and distinct cultivar of *Berberis* plant named 'Orange Dream' as herein illustrated and described.

* * * * *